United States Patent [19] [11] 3,950,330
Treuner et al. [45] Apr. 13, 1976

[54] 3-ALKYLTHIO AND 3-HETEROTHIO DERIVATIVES OF [[(THIOALKOXY)THIOCARBONYL]OX-Y]ACETYL CEPHALOSPORINS

[75] Inventors: Uwe D. Treuner; Hermann Breuer, both of Regensburg, Germany

[73] Assignee: E. R. Squibb & Sons, Inc., Princeton, N.J.

[22] Filed: Dec. 18, 1974

[21] Appl. No.: 533,900

[52] U.S. Cl. .............................. 260/243 C; 424/246
[51] Int. Cl.² ....................................... C07D 501/20
[58] Field of Search .............................. 260/243 C

[56] References Cited
UNITED STATES PATENTS
3,812,116  5/1974  Takano et al. .................. 260/243 C Primary Examiner—Nicholas S. Rizzo
Attorney, Agent, or Firm—Lawrence S. Levinson; Merle J. Smith

[57] ABSTRACT
3-Alkylthio- and 3-heterothio derivatives of [[(thioalkoxy)thiocarbonyl]oxy]acetylcephalosporins having the general formula

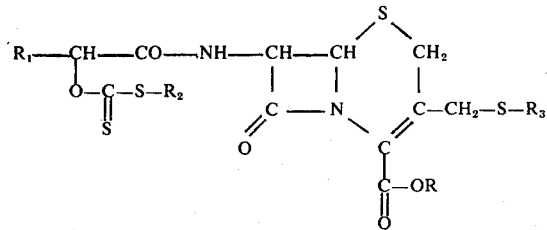

wherein R is hydrogen, lower alkyl, phenyl-lower alkyl, tri(lower alkyl)stannyl, tri(lower alkyl)silyl, a salt forming ion or the group

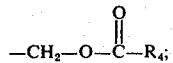

$R_1$ is hydrogen, lower alkyl, phenyl, pyridyl, thienyl or furyl; $R_2$ is lower alkyl or phenyl-lower alkyl; $R_3$ is lower alkyl, a five-membered heterocycle containing only nitrogen and carbon or nitrogen, carbon and oxygen or sulfur in the ring or pyridine-N-oxide; $R_4$ is lower alkyl, phenyl or phenyl-lower alkyl; are useful as antibacterial agents.

11 Claims, No Drawings

3-ALKYLTHIO AND 3-HETEROTHIO DERIVATIVES OF [[(THIOALKOXY)THIOCARBONYL]OXY] ACETYL CEPHALOSPORINS

SUMMARY OF THE INVENTION

This invention relates to new 3-alkylthio- and 3-heterothio derivatives of [[(thioalkoxy)thiocarbonyl-]oxy]acetylcephalosporins having the formula (I)

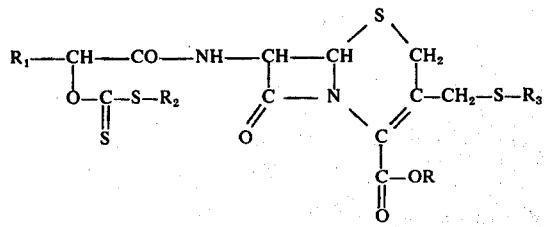

R represents hydrogen, lower alkyl, phenyl-lower alkyl, tri(lower alkyl)stannyl, tri(lower alkyl)silyl, a salt forming ion or the group

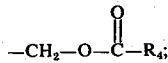

$R_1$ represents hydrogen, lower alkyl, phenyl, pyridyl, thienyl or furyl; $R_3$ represents lower alkyl, a five membered heterocyclic ring system including thiadiazolyl, oxadiazolyl or triazolyl, tetrazolyl, or pyridine-N-oxide; $R_2$ represents lower alkyl or phenyl-lower alkyl; and $R_4$ represents lower alkyl, phenyl or phenyl-lower alkyl. The heterocyclic groups represented by $R_1$ and $R_3$, respectively, optionally bear a lower alkyl group, preferably methyl. They are then $R_5$-pyridyl, $R_5$-thienyl, $R_5$-furyl, $R_5$-thiadiazolyl, $R_5$-oxadiazolyl, $R_5$-triazolyl, $R_5$-tetrazolyl or $R_5$-1-oxopyridinyl, wherein $R_5$ is hydrogen or lower alkyl.

The preferred members within each group are as follows: R is hydrogen, phenyl-lower alkyl, alkali metal, trimethylsilyl or

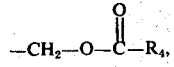

especially hydrogen, methyl, pivaloyloxymethyl, sodium or potassium; $R_1$ is hydrogen, lower alkyl, phenyl or thienyl, especially hydrogen or phenyl; $R_2$ is lower alkyl, especially methyl or ethyl; $R_3$ is lower alkyl, especially methyl, (lower alkyl)thiadiazolyl, especially methylthiadiazolyl, tetrazolyl, (lower alkyl)tetrazolyl, especially methyltetrazolyl; and $R_4$ is methyl or t-butyl.

DETAILED DESCRIPTION OF THE INVENTION

The various groups represented by the symbols have the meanings defined below and these definitions are retained throughout this specification.

The lower alkyl groups are the straight and branched chain hydrocarbon groups in the series from methyl to heptyl, metyl and ethyl being preferred.

The phenyl-lower alkyl radicals include a phenyl ring attached to a lower alkyl group of the kind described above as well as those containing two phenyl groups such as benzhydryl.

The salt forming ions represented by R are metal ions, e.g., alkali metal ions such as sodium or potassium, alkaline earth metal ions such as calcium or magnesium, or an amine salt ion, e.g., a (lower alkyl)amine like methylamine or triethylamine, etc.

The heterocyclic groups represented by $R_3$ are the five membered nitrogen heterocyclics thiadiazole, oxadiazole, or tetrazole or pyridine-N-oxide and their lower alkyl substituted analogs including 1,2,4-thiadiazol-5-yl, 1,2,4-thiadiazol-3-yl, 1,3,4-thiadiazol-2-yl, 1,3,4-oxadiazol-2-yl, 1,2,4-triazol-3-yl, 1,2,3-triazol-4-yl, tetrazolyl, 1-oxopyridinyl as well as those radicals bearing a lower alkyl group, especially methyl.

The new 3-alkyl- and 3-heterothio-[[(thioalkoxy)thiocarbonyl]oxy]acetylcephalosporins of this invention are produced by reacting a 7-aminocephalosporanic acid compound of the formula (II)

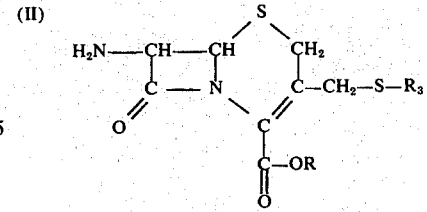

with a [[(thioalkoxy)thiocarbonyl]oxy]acetic acid of the formula (III)

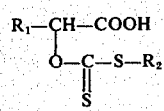

or an activated derivative of (III).

The activated derivatives referred to include, for example, the reaction product with an anhydride forming reagent such as ethylchloroformate, benzoyl chloride, pivaloyl chloride, etc., or with bis-imidazolecarbonyl, dicyclohexylcarbodiimide, p-nitrophenol or the like.

The reaction between the 7-aminocephalosporanic acid compound and the [[(thioalkoxy)thiocarbonyl-]oxy]acetic acid is effected, for example, by dissolving or suspending the latter or its acid chloride or acid anhydride in an inert organic solvent such as chloroform, acetone, tetrahydrofuran, methylene chloride, dioxane, benzene or the like, and adding, at a reduced temperature of about 0°–5°C, about an equimolar amount of the 7-ACA compound. An activating compound such as dicyclohexylcarbodiimide may be used. Preferably the compound of formula II is in the form of the trimethylsilyl ester. The product of the reaction is then isolated by conventional procedures, e.g., by concentration or evaporation of the solvent. The acid chloride is obtained from the acid of formula III by reaction with a chlorinating agent like thionyl chloride. If a derivative of the 7-aminocephalosporanic acid compound, such as the benzhydryl ester is used, the free acid is obtained by hydrolysis, e.g., with trifluoroacetic acid or the like. Salts are then derived from the free acid.

The 7-ACA derivative of formula II is produced by reacting 7-ACA or its derivative (wherein R has the other meanings described above) with a mercaptan HS-R$_3$ at a pH of about 8 – 8.5. This reaction can also be effected after acylation of 7-ACA with the [[(thioalkoxy)thiocarbonyl]oxy]acetic acid of formula III. The starting material for the latter sequence are described in our copending application Ser. No. 533,901 filed simultaneously herewith.

When R is the acyloxymethyl group

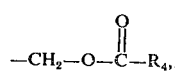

this group is introduced into the 7-aminocephalosporanic acid moiety prior to the reaction with the [[(thioalkoxy)thiocarbonyl]oxy]acetic acid or the activated derivative by treatment with one to two moles of a halomethyl ester of the formula (IV)

$$hal\text{-}CH_2OCOR_4$$

wherein hal is halogen, preferably chlorine or bromine, in an inert organic solvent such as dimethylformamide, acetone, dioxane, benzene or the like, at about ambient temperature or below.

The [[(thioalkoxy)thiocarbonyl]oxy]acetic acid of formula III is produced by forming an ester derivative of an α-hydroxyacetic acid of the formula (V)

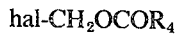

for example, by reaction with a dialkylhalosilane like dimethylchlorosilane [ClSiH(CH$_3$)$_2$] in the presence of a basic agent like triethylamine in an organic solvent like chloroform. The disilyl derivative of the formula (VI)

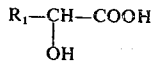

is made to react with a dithiochloroformic acid alkyl ester of the formula (VII)

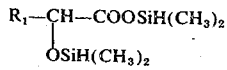

and the ester group is then removed, e.g., by hydrolysis to obtain the compound of formula III. This is then used for the acylation of the 7-aminocephalosporanic acid compound of formula II.

Alternatively the hydroxyacetic acid of formula V can be treated with carbon disulfide and a basic agent like potassium hydroxide in dimethylsulfoxide, then further treated with an iodide R$_2$I and water.

Further process details are also provided in the illustrative examples.

Certain of the compounds of this invention may exist in different optically active forms. The various stereoisomeric forms as well as the racemic mixtures are within the scope of the invention.

The compounds of this invention have a broad spectrum of antibacterial activity against both gram positive and gram negative organisms such as *Staphylococcus aureus, Salmonella schottmuelleri, Pseudomonas aeruginosa, Proteus vulgaris, Escherichia coli* and *Streptococcus pyogenes.*

They may be used as antibacterial agents in a prophylactic manner, e.g., in cleaning or environmental disinfecting compositions, or otherwise to combat infections due to organisms such as those named above, and in general may be utilized in a manner similar to cephradine and other cephalosporins. For example, a compound of formula I or a physiologically acceptable salt thereof can be used in various animal species in an amount of about 1 to 75 mg/kg, daily, orally or parenterally, in single or two to four divided doses to treat infections of bacterial origin, e.g., 4.0 mg/kg is effective in mice.

Up to about 600 mg. of a compound of formula I or a physiologically acceptable salt thereof can be incorporated in an oral dosage form such as tablets, capsules or elixirs or in an injectable form in a sterile aqueous vehicle prepared according to conventional pharmaceutical practice.

The following examples are illustrative of the invention. All temperatures are in degrees celsius. Additional variations are produced in the same manner by appropriate substitution in the starting material.

EXAMPLE 1

DL-α-[(Methylthio)thioxomethoxy]benzeneacetic acid a. 4.56 g. (30 mM) of DL-mandelic acid are boiled at reflux temperature for 3 hours together with 6.1 g. (60 mM) of triethylamine and 9.4 g. (100 mM) of dimethylchlorsilane in 150 ml. of absolute chloroform. After filtration, the filtered solution is evaporated in an oil vacuum. The crude O,O-bisdimethylsilyl derivative of the mandelic acid is obtained in the form of a pale yellow oil. This is dissolved in 50 ml. of methylene chloride and 13 g. of dithiochloroformic acid methyl ester are added. Two drops of dimethylchlorsilane are then added and the whole is kept at reflux temperature for 3 hours. After cooling, the solvent and the excess dithiochloroformic acid methyl ester are removed in vacuum. The residue is dissolved in 100 ml. of ether and the ether solution is stirred for 30 minutes with 100 ml. of 0.5 N hydrochloric acid at 0°–5°. After washing twice with 50 ml. of water, drying over sodium sulfate and evaporating, 2.3 g. of a thick oil are obtained from the organic phase which crystallizes partly after two days. The crystals are recrystallized from benzol/cyclohexane. 0.5 g. of DL-α-[(methylthio)thioxomethoxy]benzeneacetic acid are obtained in the form of white crystals, m.p. 109°–110°.

b. 4.56 g. (30 mM) of DL-mandelic acid are dissolved in 100 ml. of carbon disulfide and 3.37 g. (60 mM) of pulverized potassium hydroxide are added all at once. Absolute dimethylsulfoxide is then added with stirring until a clear solution is obtained. The whole is stirred for 1 hour and then 4.26 g. (30 mM) of methyl iodide are added. After 4 hours, the carbon disulfide is removed in vacuum and the oily residue is dissolved in 200 ml. of water. The aqueous solution is extracted three times with 50 ml. of ether. After cooling the aqueous phase to 5°, it is acidified with 2N hydrochloric acid and extracted with ether. From the ether 3.1 g. of crude DL-α-[(methylthio)thioxomethoxy]benzeneacetic acid is obtained. Recrystallization from benzol/cyclohexane yields 2.7 g., m.p. 109°–110°.

EXAMPLE 2

3-[[(5-Methyl-1,3,4-thiadiazol-2-yl)thio]methyl]-7-amino-8-oxo-5-thia-1-azabicyclo[4.2.0]oct-2-ene-2-carboxylic acid A mixture of 13.6 g. (0.05 M) of 7-aminocephalosporanic acid in 100 ml. of water and 50 ml. of acetone are brought to pH 8 with sodium hydroxide while stirring. 9.8 g. (0.57 M) of 3-methyl-1,3,4-thiadiazole-5-thiol are added and the mixture is heated at 80° for 4 hours. After cooling to 5°, this is acidified to pH 3.5 with dilute hydrochloric acid and stirred for 15 minutes. The precipitated solid is filtered under suction and washed with acetone. This 3[[(5-methyl-1,3,4-thiadiazol-2-yl)thio]methyl]-7-amino-8-oxo-5-thia-1-azabicyclo[4.2.0]oct-2-ene-2-carboxylic acid is purified by dissolving in sodium bicarbonate solution and reprecipitating with 2N hydrochloric acid; yield 12.7 g., m.p. 206°.

EXAMPLE 3

By substituting 3-methyl-1,2,4-thiadiazole-5-thiol for the 2-methyl-1,3,4-thiadiazole-5-thiol in the procedure of Example 2, 11.6 g. of 3-[[(3-methyl-1,2,4-thiadiazol-5-yl)thio]methyl]-7-amino-8-oxo-5-thia-1-azabicyclo[4.2.0]oct-2-ene-2-carboxylic acid, m.p. 186° (dec.) are obtained.

EXAMPLE 4

By substituting 1-methyl-1H-tetrazole-5-thiol for the 2-methyl-1,3,4-thiadiazole-5-thiol in the procedure of Example 2, 3-[[(1-methyl-1H-tetrazol-5-yl)thio]methyl]-7-amino-8-oxo-5-thia-1-azabicyclo[4.2.0]oct-2-ene-2-carboxylic acid is obtained.

EXAMPLE 5

3-[[(1-Methyl-1H-tetrazol-5-yl)thio]methyl]-7β-[[[(methylthio)thioxomethoxy]phenylacetyl]amino]-8-oxo-5-thia-1-azabicyclo[4.2.0]oct-2-ene-2-carboxylic acid 6.4 g. (20 mM) of 3-[[(1-methyl-1H-tetrazol-5-yl)thio]methyl]-7-aminocephalosporanic acid are suspended in 100 ml. of absolute tetrahydrofuran and heated at reflux remperature with 3.2 g. (22 mM) of hexamethyldisilazane for 1 hour. A clear solution is formed which is added dropwise at 5° to a reaction mixture of 4.7 g. (20 mM) of DL-α-[(methylthio)thioxomethoxy]benzeneacetic acid and 4.05 g. (20 mM) of dicyclohexylcarbodiimide in 100 ml. of tetrahydrofuran. After 24 hours of stirring at −5° the mixture is filtered and the filtrate evaporated. The crude trimethylsilyl ester of 3-[[(methyl-1H-tetrazol-5-yl)thio]methyl]-7β-[[[(methylthio)thioxomethoxy]phenylacetyl]amino]-8-oxo-5-thia-1-azabicyclo[4.2.0]-oct-2-ene-2-carboxylic acid forms as an oil. By treating the ester with water, the free acid of 3-[[(1-methyl-1H-tetrazol-5-yl)thio]methyl]-7β-[[[(methylthio)thioxomethoxy]phenylacetyl]amino]-8-oxo-5-thia-1-azabicyclo[4.2.-0]oct-2-ene-2-carboxylic acid is obtained, yield 2.5 g., beige powder. After recrystallization from methylene chloride-petroleum ether, the yield is 1.2 g., m.p. 131° (dec.).

EXAMPLE 6

3-[[(1-methyl-1H-tetrazol-5-yl)thio]methyl]-7β-[[[(methylthio)thioxomethoxy]phenylacetyl]amino]-8-oxo-5-thia-1-azabicyclo[4.2.0]oct-2-ene-2-carboxylic acid, potassium salt 3-[[(1-Methyl-1H-tetrazol-5-yl)thio]methyl]-7β-[[[(methylthio)thioxomethoxy]phenylacetyl]amino]-8-oxo-5-thia-1-azabicyclo[4.2.0]oct-2-ene-2-carboxylic acid, potassium salt is obtained by freeze drying a molecularly equivalent solution of the acid of Example 5 and potassium bicarbonate. A beige powder is obtained, m.p. 195° (dec.).

The following additional products are obtained by the procedure of Example 2 and 5, by substituting for the 3-methyl-1,3,4-thiadiazole-5-thiol in Example 2, the thiol indicated by the 3-substituent, and for the DL-α-[(methylthio)thioxomethoxy]benzeneacetic acid in Example 5, the acid indicated by the 7-substituent:

| Example | |
|---|---|
| 7 | 3-[[(1,3,4-thiadiazol-2-yl)thio]methyl]-7β-[2-[[(methylthio)thioxomethoxy]phenylacetyl]amino]-8-oxo-5-thia-1-azabicyclo[4.2.0]oct-2-ene-2-carboxylic acid. |
| 8 | 3-[[(1,3,4-thiadiazol-2-yl)thio]methyl]-7β-[2-[[(ethylthio)thioxomethoxy]phenylacetyl]amino]-8-oxo-5-thia-1-azabicyclo[4.2.0]oct-2-ene-2-carboxylic acid. |
| 9 | 3-[[(5-ethyl-1,3,4-thiadiazol-2-yl)thio]methyl]-7β-[2-[[(n-butylthio)thioxomethoxy]phenylacetyl]amino]-8-oxo-5-thia-1-azabicyclo[4.2.0]oct-2-ene-2-carboxylic acid and sodium salt. |
| 10 | 3-[[(5-methyl-1,3,4-thiadiazol-2-yl)thio]methyl]-7β-[[(methylthio)thioxomethoxy]acetylamino]-8-oxo-5-thia-1-azabicyclo[4.2.0]oct-2-ene-2-carboxylic acid and potassium salt. |
| 11 | 3-[[(1,2,4-triazol-3-yl)thio]methyl]-7β-[2-[[(methylthio)thioxomethoxy]phenylacetyl]amino]-8-oxo-5-thia-1-azabicyclo[4.2.0]oct-2-ene-2-carboxylic acid. |
| 12 | 3-[[(5-methyl-1,2,4-triazol-3-yl)thio]methyl]-7β-[2-[[(methylthio)thioxomethoxy]phenylacetyl]amino]-8-oxo-5-thia-1-azabicyclo[4.2.0]oct-2- | ene-2-carboxylic acid.
13. 3-[[(1,2,3-triazol-5-yl)thio]methyl]-7β-[2-[[(ethylthio)thioxomethoxy]-2-(2-thienyl)acetyl]amino]-8-oxo-5-thia-1-azabicyclo[4.2.0]oct-2-ene-2-carboxylic acid.
14. 3-[[(1-methyl]-1,2,3-triazol-5-yl)thio]methyl-7β-[2-[[(methylthio)thioxomethoxy]acetyl]amino]-8-oxo-5-thia-1-azabicyclo[4.2.0]oct-2-ene-2-carboxylic acid.
15. 3-[[(1H-tetrazol-5-yl)thio]methyl]-7β-[2-[[(benzylthio)thioxomethoxy]phenylacetyl]amino] -8-oxo-5-thia-1-azabicyclo[4.2.0]oct-2-ene-2-carboxylic acid.
16. 3-[[(1-ethyl-1H-tetrazol-5-yl)thio]methyl]7β-[2-[[(methylthio)thioxomethoxy]acetyl]amino]-8-oxo-5-thia-1-azabicyclo[4.2.0]oct-2-ene-2-carboxylic acid, trimethylsilyl ester.
17. 3-[[(1,2,4-triazol-3-yl)thio]methyl]-7β-[2-[[(methylthio)thioxomethoxy]-2-(2-furyl)acetyl]amino]-8-oxo-5-thia-1-azabicyclo[4.2.0]oct-2-ene-2-carboxylic acid.
18. 3-[[(5-methyl-1,3,4-thiadiazol-2-yl)thio]methyl]-7β-[2-[[(methylthio)thioxomethoxy]-2-(2-pyridyl)acetyl]amino]-8-oxo-5-thia-1-azabicyclo[4.2.0]oct-2-ene-2-carboxylic acid and potassium salt.
19. 3-[[(1,2,4-thiadiazol-5-yl)thio]methyl]-7β-[2-[[(n-propylthio)thioxomethoxy]acetyl]amino]-8-oxo-5-thia-1-azabicyclo[4.2.0]oct-2-ene-2-carboxylic acid, trimethylsilyl ester.
20. 3-[[(1,2,4-thiadiazol-3-yl)thio]methyl]-7β-[2-[[(phenylethylthio)thioxomethoxy]phenylacetyl]amino]-8-oxo-5-thia-1-azabicyclo[4.2.0]oct-2-ene-2-carboxylic acid.
21. 3-[[(5-butyl-1,2,4-thiadiazol-3-yl)thio]methyl]-7β-[2-[[(methylthio)thioxomethoxy]acetyl]amino]-8-oxo-5-thia-1-azabicyclo[4.2.0]oct-2-ene-2-carboxylic acid.
22. 3-[(methylthio)methyl]-7β-[2-[[(methylthio)thioxomethoxy]phenylacetyl]amino]-8-oxo-5-thia-1-azabicyclo[4.2.0]-oct-2-ene-2-carboxylic acid methyl ester.
23. 3-[(ethylthio)methyl]-7β-[[(methylthio)thioxomethoxy]phenylacetyl]amino]-8-oxo-5-thia-1-azabicyclo[4.2.0]oct-2-ene-2-carboxylic acid.
24. 3-[(methylthio)methyl]-7β-[2-[[(methylthio)thioxomethoxy]acetyl]amino]-8-oxo-5-thia-1-azabicyclo[4.2.0]oct-2-ene-2-carboxylic acid and sodium salt.
25. 3-[(ethylthio)methyl]-7β-[2-[[ (ethylthio)thioxomethoxy]acetyl]amino]-8-oxo-5-thia-1-azabicyclo[4.2.0]-oct-2-ene-2-carboxylic acid and triethylamine salt.
26. 3-[(methylthio)methyl]-7β-[2-[[(methylthio)thioxomethoxy]-2-(2-thienyl)acetyl]amino]-8-oxo-5-thia-1-azabicyclo[4.2.0]oct-2-ene-2-carboxylic acid, benzhydryl ester and free acid.
27. 3-[(ethylthio)methyl]-7β-[[[(methylthio)thioxomethoxy]-2-(3-furyl)acetyl]amino]-8-oxo-5-thia-1-azabicyclo[4.2.0]oct-2-ene-2-carboxylic acid.
28. 3-[(methylthio)methyl]-7β-[2-[[(methylthio)thioxomethoxy]-2-(2-pyridyl)acetyl]amino]-8-oxo-5-thia-1-azabicyclo[4.2.0]oct-2-ene-2-carboxylic acid.
29. 3-[(propylthio)methyl]-7β-[2-[[(methylthio)thioxomethoxy]phenylacetyl]amino]-8-oxo-5-thia-1-azabicyclo[4.2.0]oct-2-ene-2-carboxylic acid.
30. 3-[[(1-ethyl-1H-tetrazol-5-yl)thio]methyl]-7β-[2-[[(ethylthio)thioxomethoxy]-2-(2-pyridyl)acetyl]amino]-8-oxo-5-thia-1-azabicyclo[4.2.0]oct-2-ene-2-carboxylic acid and potassium salt.
31. 3-[[(1H-tetrazol-5-yl)thio]methyl]-7β-[2-[[(methylthio)thioxomethoxy]acetyl]amino]-8-oxo-5-thia-1-azabicyclo[4.2.0]oct-2-ene-2-carboxylic acid.
32. 3-[[(1-methyl-1H-tetrazol-5-yl)thio]methyl]-7β-[2-[[(ethylthio)thioxomethoxy]-2-(2-furyl)acetyl]amino]-8-oxo-5-thia-1-azabicyclo[4.2.0]oct-2-ene-2-carboxylic acid and potassium salt.
33. 3-[[(1-methyl-1H-tetrazol-5-yl)thio]methyl]-7β-[2-[[(methylthio)thioxomethoxy]-2-(3-thienyl)acetyl]amino]-8-oxo-5-thia-1-azabicyclo[4.2.0]oct-2-ene-2-carboxylic acid pivaloyloxymethyl ester.
34. 3-[[(1-ethyl-1H-tetrazol-5-yl)thio]methyl]-7β-[2-[[(ethylthio)thioxomethoxy]acetyl]amino] -8-oxo-5-thia-1-azabicyclo[4.2.0]oct-2-ene-2-carboxylic acid.
35. 3-[[(1H-tetrazol-5-yl)thio]methyl]-7β-[2-[n-butylthio)thioxomethoxy]acetyl]amino]-8-oxo-5-thia-1-azabicyclo[4.2.0]oct-2-ene-2-carboxylic acid and phenylacetoxymethyl ester.
36. 3-[[(3-methyl-1,2,4-thiadiazol-5-yl)thio]methyl]-7β-[2-[[(methylthio)thioxomethoxy]phenylacetyl]amino]-8-oxo-5-thia-1-azabicyclo[4.2.0]oct-2-ene-2-carboxylic acid.
37. 3-[[(1,2,4-thiadiazol-3-yl)thio]methyl]-7β-[2-[[(methylthio)thioxomethoxy]propionyl]amino]-8-oxo-5-thia-1-azabicyclo[4.2.0]oct-2-ene-2-carboxylic acid pivaloyloxymethyl ester.

| 38 | 3-[[(1H-tetrazol-5-yl)thio]methyl]-7β-[2-[[(ethyl-thio)thioxomethoxy]propionyl]amino]-8-oxo-5-thia-1-azabicyclo[4.2.0]oct-2-ene-2-carboxylic acid. |
| 39 | 3-[[(1-methyl-1H-tetrazol-5-yl)thio]methyl]-7β-[2-[[(methylthio)thioxomethoxy]butyryl]amino]-8-oxo-5-thia-1-azabicyclo[4.2.0]oct-2-ene-2-carboxylic acid and potassium salt. |
| 40 | 3-[[(1-oxopyridin-2-yl)thio]methyl]-7β-[2-[[(methyl-thio)thioxomethoxy]phenylacetyl]amino]-8-oxo-5-thia-1-azabicyclo[4.2.0]oct-2-ene-2-carboxylic acid. |
| 41 | 3-[[(4-methyl]-1-oxopyridin-2-yl)thio]methyl-7β-[2-[[(methylthio)thioxomethoxy]propionyl]amino]-8-oxo-5-thia-1-azabicyclo[4.2.0]oct-2-ene-2-carboxylic acid and sodium salt. |
| 42 | 3-[[1,3,4-oxadiazol-2-yl)thio]methyl]-7β-[2-[[(methyl-thio)thioxomethoxy]phenylacetyl]amino]-8-oxo-5-thia-1-azabicyclo[4.2.0]oct-2-ene-2-carboxylic acid. |
| 43 | 3-[[5-methyl-1,3,4-oxadiazol-2-yl)thio]methyl-7β-[2-[[(methylthio)thioxomethoxy]n-butyryl]amino]-8-oxo-5-thia-1-azabicyclo[4.2.0]oct-2-ene-2-carboxylic acid. |

What is claimed is:

1. A compound of the formula

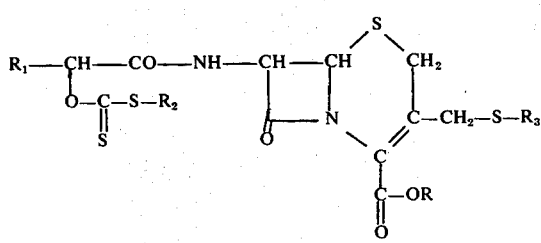

wherein R is hydrogen, lower alkyl, phenyl-lower alkyl, tri(lower alkyl)stannyl, tri(lower alkyl)silyl, -CH$_2$OCO-R$_4$, alkali metal, alkaline earth metal or (lower alkyl)amine; R$_1$ is hydrogen, lower alkyl, phenyl, R$_5$-pyridyl, R$_5$-thienyl or R$_5$-furyl; R$_2$ is lower alkyl or phenyl-lower alkyl; R$_3$ is a five membered heterocyclic of the group R$_5$-thiadiazole, R$_5$-triazole, R$_5$-oxadiazole or R$_5$-tetrazole; R$_4$ is lower alkyl, phenyl or phenyl-lower alkyl; and R$_5$ is hydrogen or lower alkyl.

2. A compound as in claim 1 wherein R is hydrogen, phenyl-lower alkyl, alkali metal, trimethylsilyl or

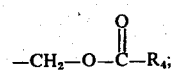

R$_1$ is hydrogen, lower alkyl, phenyl or thienyl; R$_2$ is lower alkyl; R$_3$ is tetrazole or (lower alkyl)tetrazole; and R$_4$ is methyl or t-butyl.

3. A compound as in claim 1 wherein R$_1$ is phenyl.

4. A compound as in claim 3 wherein R$_2$ is lower alkyl.

5. A compound as in claim 3 wherein R$_2$ is lower alkyl and R$_3$ is (lower alkyl)tetrazole.

6. A compound as in claim 5 wherein each lower alkyl group is methyl.

7. A compound as in claim 1 wherein R$_3$ is 1-lower alkyl-1H-tetrazol-5-yl.

8. A compound as in claim 1 wherein R is hydrogen, R$_1$ is phenyl, R$_2$ is methyl and R$_3$ is 1-methyl-1H-tetrazol-5-yl.

9. Alkali metal salt of the compound of claim 8.

10. A compound as in claim 9 wherein the alkali metal is potassium.

11. A compound as in claim 1 wherein R is hydrogen, R$_1$ is phenyl, R$_2$ is methyl and R$_3$ is 3-methyl-1,2,4-thiadiazol-5-yl.

* * * * *